United States Patent
Herr et al.

(10) Patent No.: US 11,723,581 B2
(45) Date of Patent: Aug. 15, 2023

(54) ELECTROMYOGRAPHY SENSOR

(71) Applicant: Massachusetts Institute of Technology, Cambridge, MA (US)

(72) Inventors: Hugh M. Herr, Somerville, MA (US); Seong Ho Yeon, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 948 days.

(21) Appl. No.: 16/661,283

(22) Filed: Oct. 23, 2019

(65) Prior Publication Data

US 2020/0121210 A1   Apr. 23, 2020

Related U.S. Application Data

(60) Provisional application No. 62/749,230, filed on Oct. 23, 2018.

(51) Int. Cl.
| | |
|---|---|
| *A61B 5/389* | (2021.01) |
| *G06F 3/01* | (2006.01) |
| *A61B 5/00* | (2006.01) |
| *A61F 2/72* | (2006.01) |
| *A61F 2/64* | (2006.01) |
| *A61F 2/66* | (2006.01) |
| *A61F 2/74* | (2006.01) |

(52) U.S. Cl.
CPC ............ *A61B 5/389* (2021.01); *A61B 5/688* (2013.01); *A61F 2/64* (2013.01); *A61F 2/6607* (2013.01); *A61F 2/72* (2013.01); *G06F 3/015* (2013.01); *A61F 2/741* (2021.08); *A61F 2002/6664* (2013.01)

(58) Field of Classification Search
CPC ................................. A61B 5/389; A61B 5/688
USPC .......................................... 345/173; 600/546
See application file for complete search history.

(56) References Cited

U.S. PATENT DOCUMENTS

| | | | |
|---|---|---|---|
| 2013/0046394 | A1 | 2/2013 | Lipschutz et al. |
| 2015/0234426 | A1* | 8/2015 | Bailey ............ A61B 5/6831 |
| | | | 427/96.1 |
| 2018/0001086 | A1 | 1/2018 | Bartholomew et al. |
| 2018/0165566 | A1* | 6/2018 | Rogers ................ G01T 1/00 |
| 2019/0015008 | A1* | 1/2019 | Alizadeh ............ A61B 5/282 |

(Continued)

FOREIGN PATENT DOCUMENTS

| | | |
|---|---|---|
| WO | WO 2016/196801 A1 | 12/2016 |
| WO | WO 2019/032118 A1 | 2/2019 |

OTHER PUBLICATIONS

International Search Report and Written Opinion for Int'l Application No. PCT/US2020/054904, titled: Electromyography Sensor, dated Mar. 26, 2021.

(Continued)

*Primary Examiner* — Calvin C Ma
(74) *Attorney, Agent, or Firm* — Hamilton, Brook, Smith & Reynolds, P.C.

(57) ABSTRACT

An electromyography (EMG) sensor for a wearable device, such as a prosthetic device attachable to a residual limb, includes a flexible substrate comprising an elongated portion and an electrode portion. At least two electrodes are disposed at a surface of the electrode portion of the flexible substrate, and leads from the at least two electrodes extend through the elongated portion of the flexible substrate.

22 Claims, 15 Drawing Sheets

(56) References Cited

U.S. PATENT DOCUMENTS

2021/0077304 A1* 3/2021 Xu .................. A61B 5/447

OTHER PUBLICATIONS

Kim, N. et al., "Stretchable Multichannel Electromyography Sensor Array Covering Large Area for Controlling Home Electronics with Distinguishable Signals from Multiple Muscles," *ACS Applied Materials & Interfaces*, 8(32): 21070-21076 (Aug. 2016).

Kim, S.J. et al., "Stretchable and Transparent Biointerface Using Cell-Sheet-Graphene Hybrid for Electrophysiology and Therapy of Skeletal Muscle," *Advances Functional Materials*, 26(19): 3207-3217 (May 2016).

Kim et al., "S-1 Supporting Information Stretchable Multichannel Electromyography Sensor Array Covering Large Area for Controlling Home Electronics with Distinguishable Signals from Multiple Muscles", Retrieved from the Internet: URL::https://pubs.acs.org/doi/abs/10.1021/acsami.6b05025#notes-1, retrieved on Jan. 15, 2021 dated Jan. 1, 2016.

Marques, D.G. et al., "Reliable interfaces for EGaIn multi-layer stretchable circuits and microelectronics," *Lab on a Chip*, 19(5): 897-906 (Jan. 2019).

D. Farina, R. Merletti, and R. M. Enoka, "The extraction of neural strategies from the surface EMG," Neural Control of Movement, *J. Appl. Physiol.*, vol. 96, No. 4, pp. 1486-1495, 2004.

P. Geethanjali, "Myoelectric control of prosthetic hands: State-of-the-art review," *Med. Devices Evid. Res.*, vol. 9, pp. 247-255, 2016.

D. Farina, S. Member, N. Jiang, H. Rehbaum, and S. Member, "The Extraction of Neural Information from the Surface EMG for the Control of Upper-Limb Prostheses : Emerging Avenues and Challenges,"Neural Syst. . . . , vol. 22, No. 4, pp. 797-809, 2014.

S. Benatti et al., "A Versatile Embedded Platform for EMG Acquisition and Gesture Recognition," *IEEE Trans. Biomed. Circuits Syst.*, vol. 9, No. 5, pp. 620-630, 2015.

B. Milosevic, S. Benatti, and E. Farella, "Design challenges for wearable EMG applications," *Proc. 2017 Des. Autom. Test Eur. DATE 2017*, pp. 1432-1437, 2017.

S. Benatti et al., "A sub-10mW real-time implementation for EMG hand gesture recognition based on a multi-core biomedical SoC," *Proc.—2017 7th Int. Work. Adv. Sensors Interfaces, IWASI 2017*, pp. 139-144, 2017.

E. Mastinu, P. Doguet, Y. Botquin, B. Hakansson, and M. Ortiz-Catalan, "Embedded System for Prosthetic Control Using Implanted Neuromuscular Interfaces Accessed Via an Osseointegrated Implant," *IEEE Trans. Biomed. Circuits Syst.*, vol. 11, No. 4, pp. 867-877, 2017.

L. J. Hargrove et al., "Robotic Leg Control with EMG Decoding in an Amputee with Nerve Transfers," *N. Engl. J. Med.*, vol. 369, No. 13, pp. 1237-1242, Sep. 2013.

S. K. Au, P. Bonato, and H. Herr, "An EMG-position controlled system for an active ankle-foot prosthesis: an initial experimental study," 2005, pp. 375-379.

A. J. Young, T. A. Kuiken, and L. J. Hargrove, "Analysis of using EMG and mechanical sensors to enhance intent recognition in powered lower limb prostheses," *J. Neural Eng.*, vol. 11, No. 5, Sep. 2014.

E. A. Clancy, D. Farina, and G. Filligoi, *Single-channel techniques for information extraction from the surface EMG signal*. 2004.

D. C. Tkach and L.J. Hargrove, "Neuromechanical sensor fusion yields highest accuracies in predicting ambulation mode transitions for trans-tibial amputees.," *Annual International Conference of the IEEE*, 2013.

L. J. Hargrove et al., "Intuitive Control of a Powered Prosthetic Leg During Ambulation," *Journal of the American Medical Association*, vol. 313, No. 22, pp. 2244-2252, Jun. 2015.

N.E. Krausz et al., "Depth Sensing for Improved Control of Lower Limb Prostheses," *IEEE Transactions on Biomedical Engineering*, vol. 62, No. 11, p. 2576-2587, 2015.

J. A. Spanias et al., "Detection of and Compensation for EMG Disturbances for Powered Lower Limb Prosthesis Control," *IEEE Transactions on Neural Systems and Rehabilitation Engineering*, vol. 24, No. 2, 2016.

E. Zheng and Q. Wang, "Noncontact Capacitive Sensing-Based Locomotion Transition Recognition for Amputees With Robotic Transtibial Prostheses," *IEEE Transactions on Neural Systems and Rehabilitation Engineering*, vol. 25, No. 2, pp. 161-170, Feb. 2017.

* cited by examiner

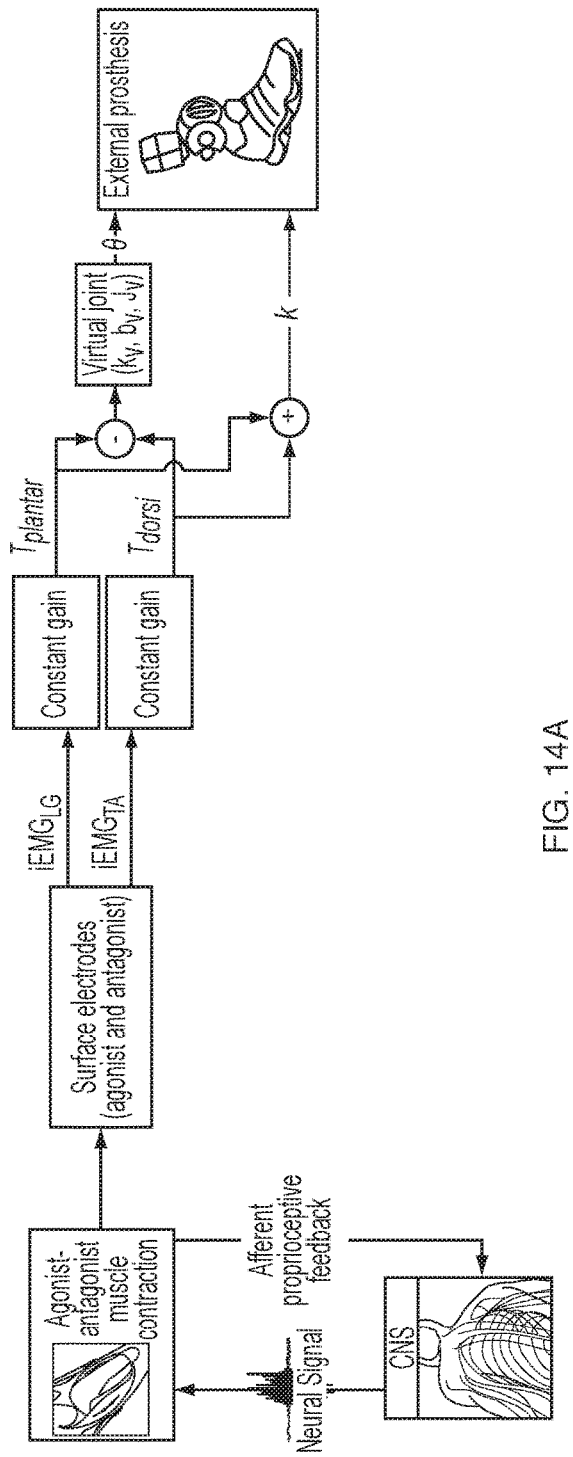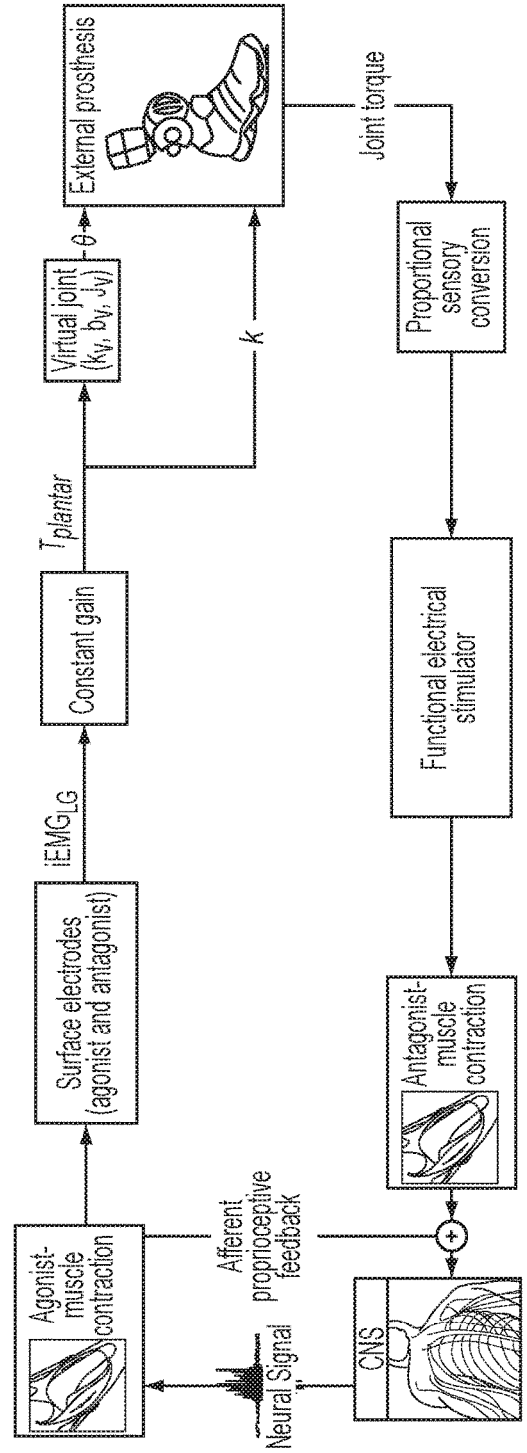
FIG. 14A
FIG. 14B

ELECTROMYOGRAPHY SENSOR

RELATED APPLICATION(S)

This application claims the benefit of U.S. Provisional Application No. 62/749,230, filed on Oct. 23, 2018. The entire teachings of the above application are incorporated herein by reference.

BACKGROUND

Electromyography (EMG) signals demonstrate collective motor unit action potentials (MUAPs) of a muscle or muscles when they fire. By analyzing EMG signals and estimated MUAPs, information can be extracted to provide for volitional control of robotic prostheses or other wearable devices.

Surface electromyography (sEMG) systems obtain EMG signals with skin surface electrodes, as opposed to fine wire electrodes that are invasively placed within muscle tissue. With sEMG systems, macroscale muscle activation at a residual limb can be estimated noninvasively, which can, in turn, be used to provide for volitional control of upper and lower extremity prostheses, exoskeletons, orthoses, and other such wearable devices.

SUMMARY

Electromyography sensors are provided that can be integrated with conventional liners, or with lower-cost custom liners, for use with prosthetic devices utilizing sEMG.

An electromyography (EMG) sensor for a wearable device, such as a prosthetic device attachable to a residual limb, includes a flexible substrate comprising an elongated portion and an electrode portion. At least two electrodes are disposed at a surface of the electrode portion of the flexible substrate, and leads from the at least two electrodes extend through the elongated portion of the flexible substrate.

The EMG sensor can be a low-profile sensor, having a thickness at the electrode portion, inclusive of the at least two electrodes, in the range of about 50 µm to about 500 µm, or of about 50 µm to about 120 µm. The electrodes can be dry, passive electrodes. Each of the electrodes can include a flexible metal layer. The flexible metal layers and the flexible substrate can conform to a skin surface. The electrodes can be disposed at a relative center-to-center distance in the range of about 1 cm to about 4 cm, or of about 1.5 cm to about 2 cm. Where more than one pair of electrodes is disposed on an electrode portion of the substrate, the electrodes of each of the pairs can be disposed at a relative center-to-center distance in the range of about 1 cm to about 4 cm, or of about 1.5 cm to about 2 cm. A diameter of each of the electrodes can be in the range of about 0.5 cm to about 1.5 cm. The EMG sensor can include a non-woven substrate. The substrate can comprise a flexible polymer, such as polyimide.

A liner for a prosthetic device includes an EMG sensor. The EMG sensor can be placed within the liner such that the electrode portion of the EMG sensor is in contact with the skin of a body segment on which the liner is worn. The EMG sensor can be affixed, removably or irremovably, to an inner surface of the liner. For example, the EMG sensor can be adhered to an inner surface of the liner, or the inner surface of the liner can include a recess configured to receive the EMG sensor. The recess can be configured to receive the electrode portion of the EMG sensor, with an elongated portion disposed along an inner surface of the liner or embedded within the liner. Alternatively, or in addition, at least one of the EMG sensor and the liner includes a fastener that is configured to fasten the EMG sensor to an inner surface of the liner. For example, the flexible substrate of the EMG sensor can include a plurality of holes configured to receive complimentary projections disposed on the inner surface of the liner. Alternatively, the flexible substrate of the EMG sensor can include projections configured to extend into recesses or receptacles disposed on the inner surface of the liner.

The elongated portion of the EMG sensor can be disposed between an inner layer and an outer layer of the liner, the elongated portion comprising a serpentine or corrugated shape configured to extend as the liner is stretched. The elongated portion can be disposed to extend over a proximal end of the liner. Alternatively, the elongated portion can be disposed to extend to a pin connection at a distal end of the liner to make electrical connection with a prosthetic device. An end of the elongated portion of the sensor can include a connector configured to engage with a portable EMG device that is in communication with a prosthetic device. The portable EMG device can be in wireless communication with the prosthetic device or can be hardwired to the prosthetic device.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 14A is a diagram illustrating a virtual joint dynamic model for the control system of FIG. 13.

FIG. 14B is a diagram illustrating another virtual joint dynamic model for the control system of FIG. 13.

DETAILED DESCRIPTION

Integration of a portable and real-time sEMG measurement system with a powered prosthetic actuator control system can provide for a portable prosthesis with neural volitional control. However, commercially-available sEMG measurement systems are typically inadequate for use with prosthetic wearable devices as such EMG systems include sensors and associated electronics disposed at the sensors that are not capable of accommodating dynamic surface loading that occurs inside a weight-bearing socket.

Figure 1:
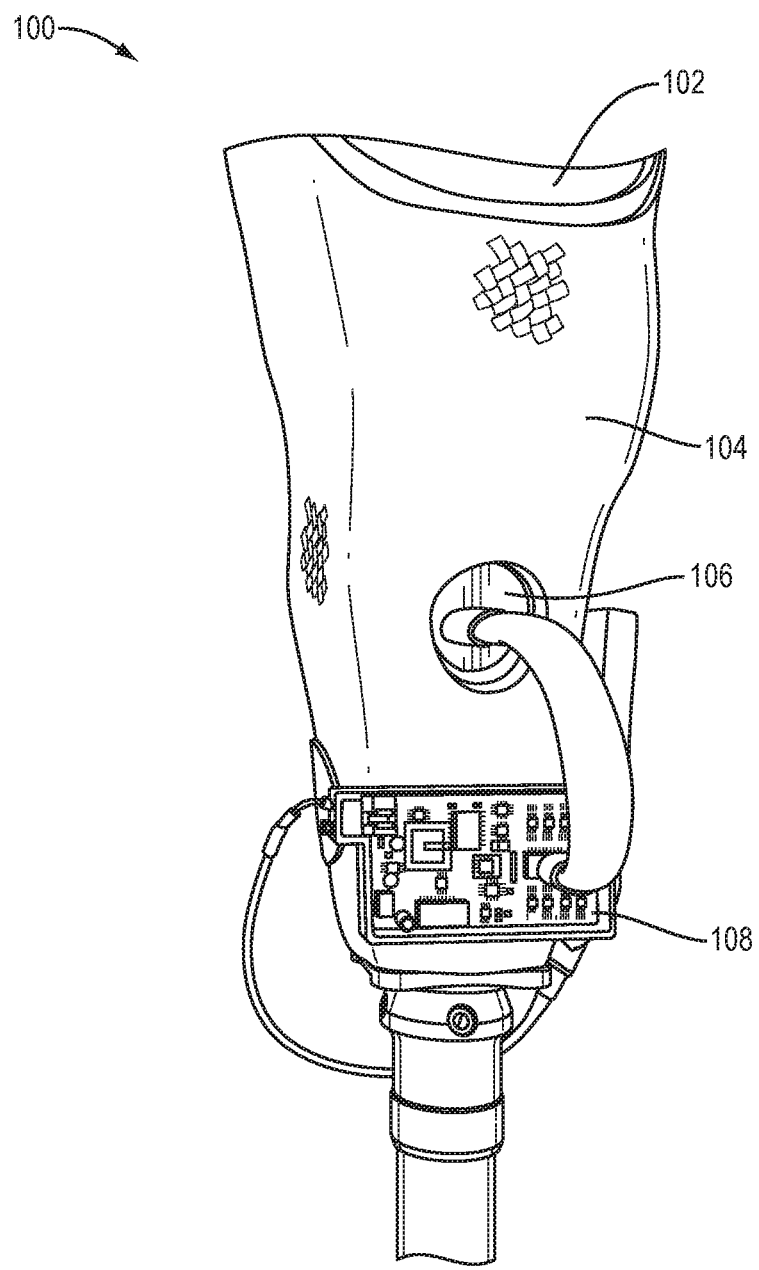
FIG. 1 shows a prior art surface electromyography (sEMG) system including a custom liner and a custom socket.

To address this issue, custom sockets and liners built for prosthetic neural interface systems have been developed. An example of a prior-art custom liner and socket having an integrated sEMG system is shown in FIG. 1. The system 100 includes a custom liner 102 having embedded conductive fabric, which provides for integrated electrodes that obtain sEMG measurements from the residual limb. The system 100 further includes a custom socket 104 having an opening 106 to provide for communicative access from the liner 102 to an sEMG board 108.

Custom liners and sockets, such as the liner and socket shown in FIG. 1, carry several disadvantages. Liners for prosthetic devices must be washed regularly and are typically replaced every few months. Liners having integrated electrodes and associated connective components can be impracticably expensive to replace every few months. Furthermore, such liners are difficult to wash, and the integrity of electrical components contained within the liner may not withstand frequent washings, thereby requiring even more frequent replacement of the liner. It is also undesirable to modify a socket to include openings to provide access to a liner. Sockets are particularly shaped to provide weight-bearing support to a residual limb, and inclusion of holes in the socket can compromise function and comfort of the socket for the wearer.

Flexible EMG sensors are provided that can be integrated with either conventional liners or lower-cost customized liners. The flexible EMG sensors can also provide for communication with other components of an sEMG system without modification of a socket.

A description of example embodiments follows.

Figure 2A:
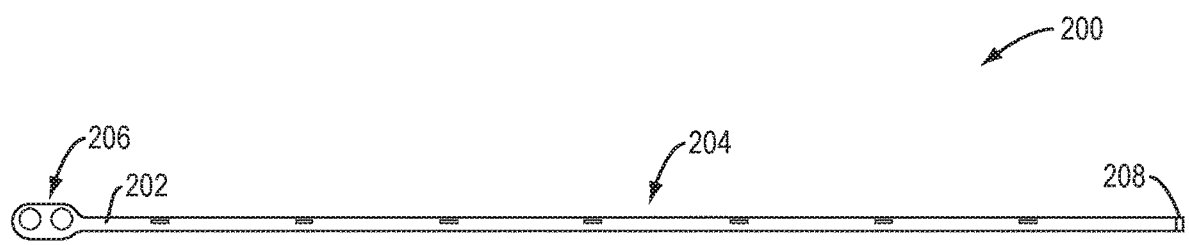
FIG. 2A is a schematic of an EMG sensor for use with a prosthetic liner and/or socket.
Figure 2B:
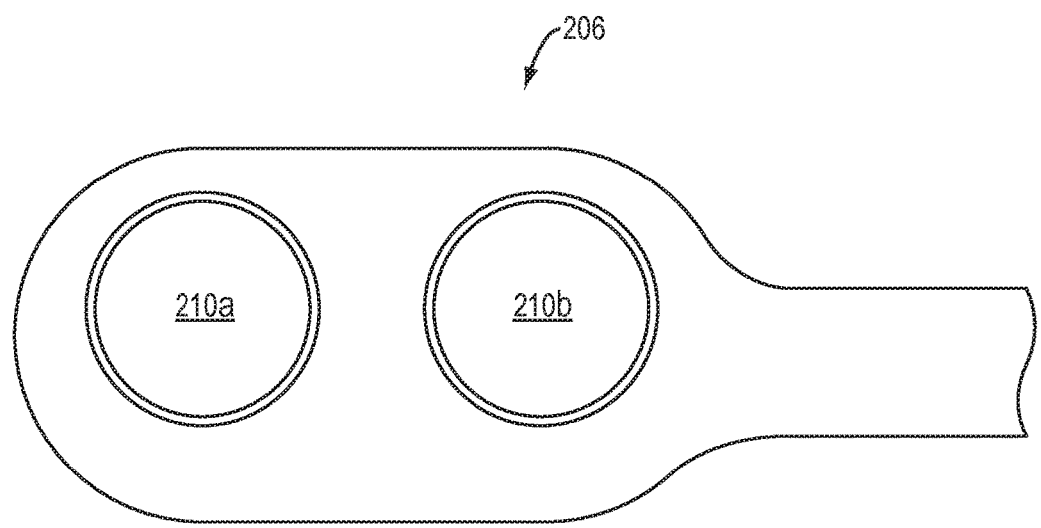
FIG. 2B shows a detailed view of an electrode portion of the EMG sensor of FIG. 2A.
Figure 2C:
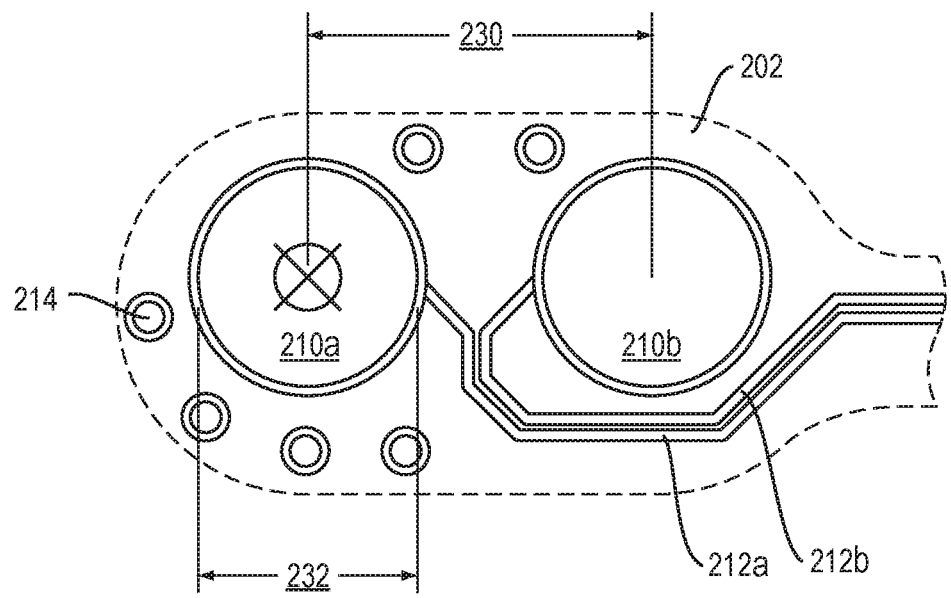
FIG. 2C shows another detailed view of an electrode portion of the EMG sensor of FIG. 2A.

An EMG sensor 200 is shown in FIGS. 2A-2C. The EMG sensor 200 includes a flexible substrate 202 forming an elongated portion 204 and an electrode portion 206. The electrode portion 206 includes two or more electrodes 210a, 210b disposed at a surface of the flexible substrate 202. Leads 212a, 212b from each of the two or more electrodes 210a, 210b extend through the elongated portion 204. The elongated portion 204 can include a connector 208 to provide for connection of the electrode leads to other devices, as described further below.

Figure 3A:
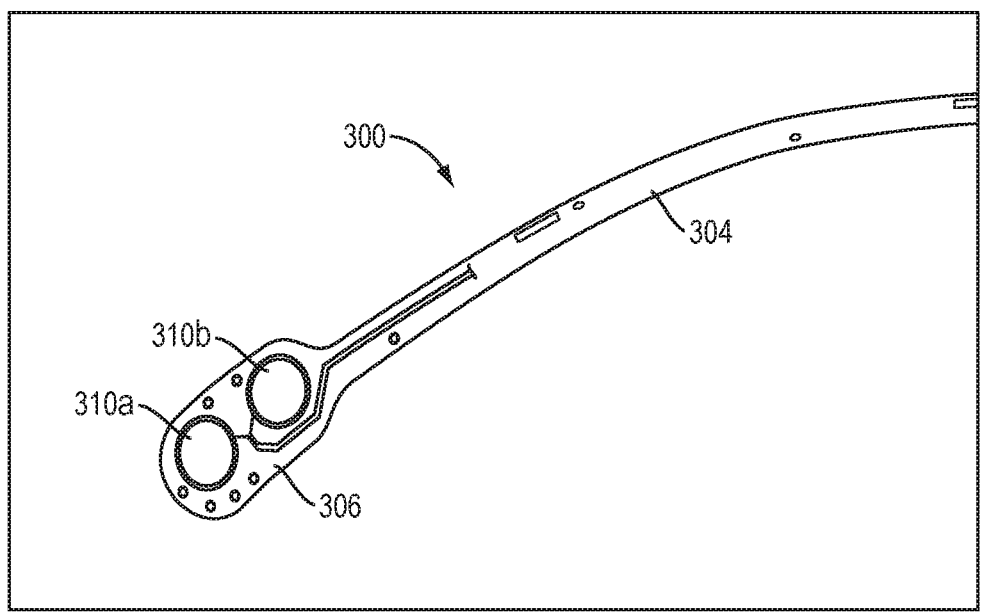
FIG. 3A shows a fabricated EMG sensor.
Figure 3B:
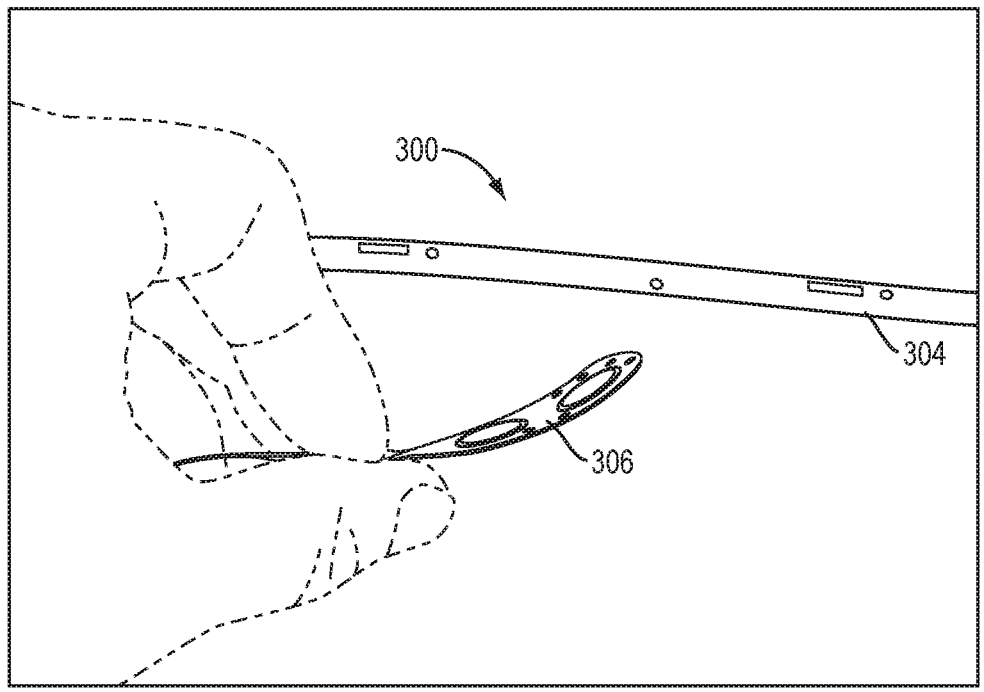
FIG. 3B shows a side view of an electrode portion of the EMG sensor of FIG. 3A.

An example of a fabricated EMG sensor 300 is shown in FIGS. 3A-3B. As is visible in FIGS. 3A-3B, the sensor 300 is a low-profile sensor of minimal thickness. A thickness of the electrode portion 306, including electrodes 310a, 310b, can be in range of about 50 µm to about 500 µm, or in range of about 50 µm to about 120 µm (e.g., 45 µm, 50 µm, 60 µm, 70 µm, 80 µm, 90 µm, 100 µm, 110 µm, 120 µm, and 125 µm). Such thicknesses can provide for unobtrusive placement atop an inner surface of a liner, or within a liner, so as to not interfere with surface loading inside the socket.

Figure 4:
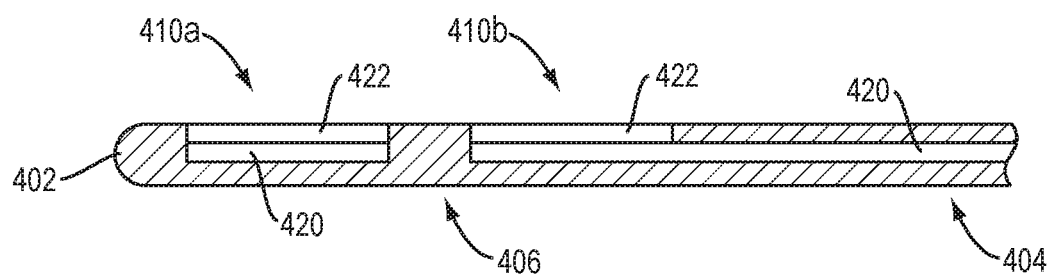
FIG. 4 shows a cross-section of an electrode portion of an EMG sensor.

The electrodes of an EMG sensor can be dry, passive electrodes. The electrodes can be formed from one or more flexible metal layers disposed within the substrate and having a contact surface that is exposed for contact with the skin. For example, a cross-section of an electrode portion 406 of an example EMG sensor is shown in FIG. 4, with the substrate 402 containing a copper layer 420 for inner electrical connection of the electrodes 410a, 410b and their respective leads. A gold-coated surface layer 422 is disposed at each of the two electrodes 410a, 410b to provide for a skin-interface surface. While copper and gold are provided as example metals, other conductive materials can instead be included within an EMG sensor. For example, inner electrical connections can be formed of other metals, and skin-interface surfaces of an EMG sensor can include thin films, conductive textiles, metal foils, and cotton, or any combination thereof.

The electrodes of an EMG sensor can be disposed within the electrode portion at a distance suitable for obtaining EMG measurements of a muscle of interest. For example, as illustrated in FIG. 2C, a relative center-to-center distance 230 of electrodes 210a, 210b can be in range of about 1 cm to about 4 cm (e.g., 0.9 cm, 1 cm, 2 cm, 3 cm, 4 cm, 4.1 cm), or in range of about 1.5 cm to about 2 cm (e.g., 1.4 cm, 1.5 cm, 1.75 cm, 2 cm, 2.1 cm). A diameter 232 of each electrode can be in range of about 0.5 cm to about 1.5 cm (e.g., 0.4 cm, 0.5 cm, 0.75 cm, 1 cm, 1.25 cm, 1.5 cm, 1.6 cm)

The substrate of an EMG sensor can be formed of a non-woven material or film capable of providing flexibility for the sensor to conform to a shape of a body segment. For example, the substrate can comprise a flexible polymer, such as polyimide, polyethylene, naphthalate (PEN), and polyetherimide (PEI). With a flexible substrate and flexible metal contacts, the EMG sensor can conform to and maintain contact with a skin surface of the body segment during wear with a liner.

Figure 5:
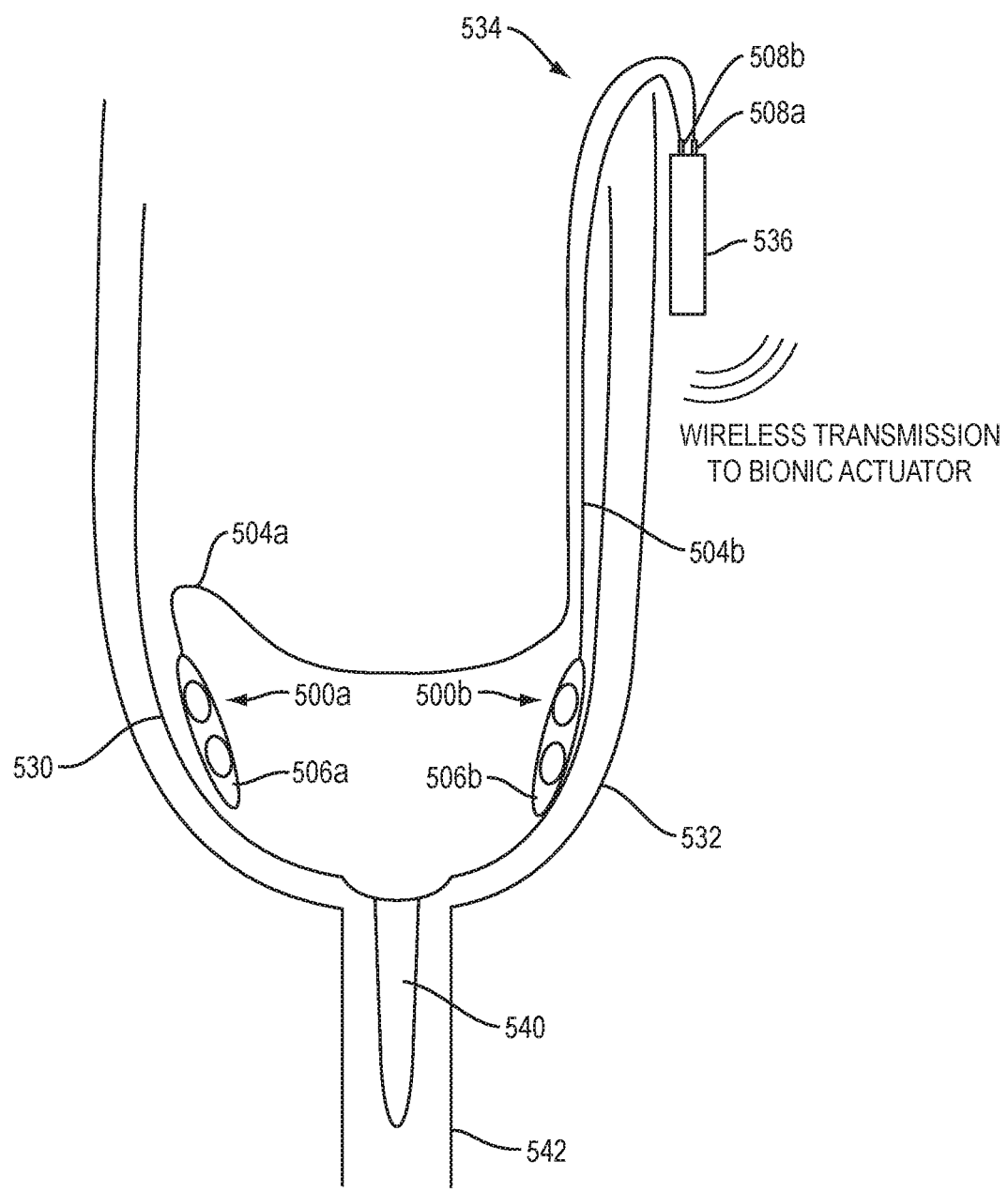
FIG. 5 is a schematic illustrating placement of an EMG sensor in a prosthetic liner.

EMG sensors, such as sensors 200, 300, can be placed within liners for prosthetic devices. As shown in FIG. 5, two flexible EMG sensors 500a, 500b are placed within an inner surface of a liner 530, which is disposed between a body segment (not shown) and a prosthetic socket 532. In particular, electrode portions 506a, 506b of the EMG sensors are disposed at locations within the liner 530 that abut muscle of the body segment from which EMG measurements are to be obtained. The elongated portions 504a, 504b of the EMG sensors are configured to extend up and over a length of the liner 530 and socket 532, with respective connectors 508a, 508b of the sensors draped over a proximal end 534 of the socket 532. For example, the elongated portion of an EMG sensor can have a length in the range of about 10 cm to about 60 cm (e.g., 9 cm, 10 cm, 15 cm, 20 cm, 30 cm, 40 cm, 50 cm, 50 cm, 51 cm). The connectors 508a, 508b can engage with a portable sEMG device 536 that contains associated front-end electronics for processing signals obtained from the sensors and/or providing wired or wireless communication with one or more actuators of a prosthetic device connected to the socket 532. Optionally, the socket 532 and/or the liner 534 includes a pin connection 540 for engaging a pylon 542 of the prosthetic device.

Figure 6A:
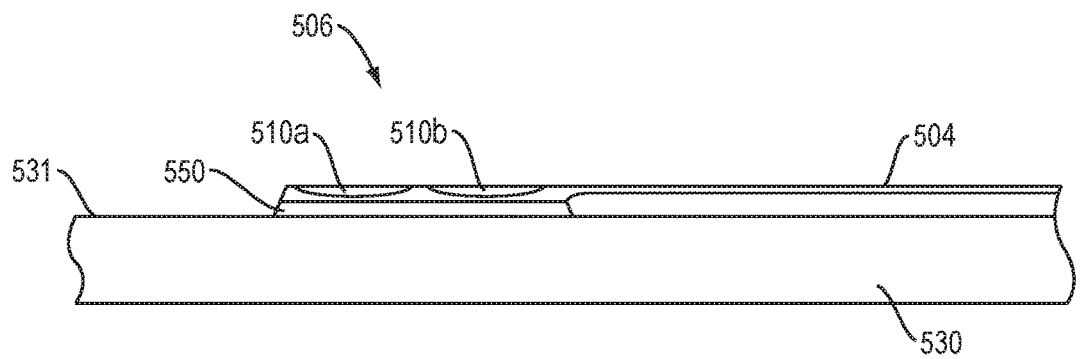
FIG. 6A shows attachment of an EMG sensor to a liner in an uncompressed state.
Figure 6B:
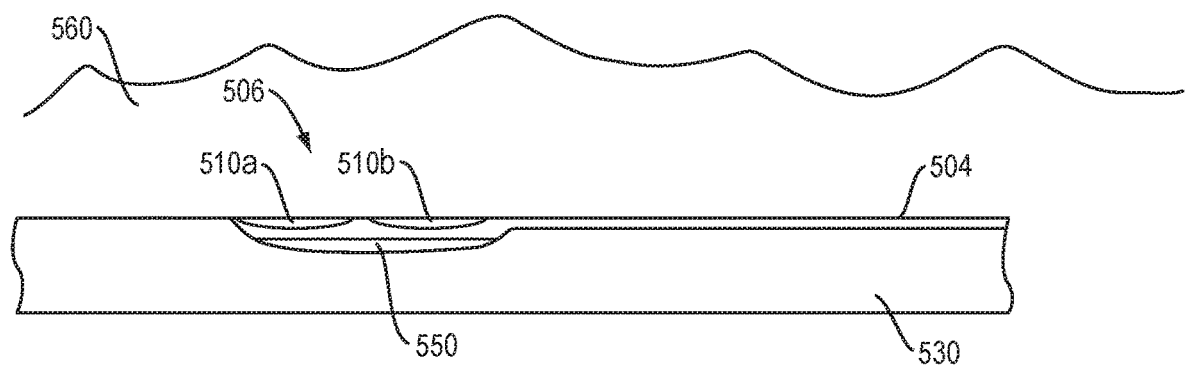
FIG. 6B shows the EMG sensor and liner of FIG. 6A in a compressed state during wear.

Such EMG sensors can be disposed within conventional liners for use with powered prosthetic devices, without requiring modification of the liner and without interfering with surface loading of the body segment to the socket. The EMG sensors can optionally be attached to an inner surface of the liner, which can assist in maintaining the EMG sensor at a desired anatomical location of the body segment during wear. For example, as shown in FIG. 6A, an adhesive layer 550 can be provided to adhere the electrode portion 506 of the sensor to an inner surface 531 of the liner 530, with electrodes 510a, 510b being exposed for skin contact. An adhesive layer can alternatively, or in addition, be provided beneath an elongated portion 504 of the sensor. Liners for prosthetic devices are typically made of flexible, cushioning materials, such as silicone and polyurethane, which provide protection to the skin and to reduce movement of a residual limb within a socket. During wear, given the compressibility of liner material and the low-profile of the EMG sensor, the sensor may indent into the liner material, providing for a flush interface with a body segment 560 when the liner 530 is being worn, as shown in FIG. 6B.

Figure 7A:
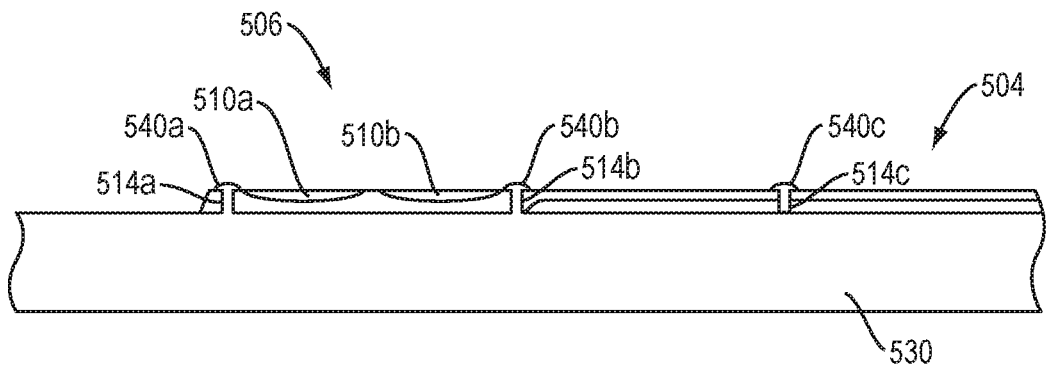
FIG. 7A shows an EMG sensor with fasteners for securing the EMG sensor to a liner.

EMG sensors can alternatively be attached to an inner surface of the liner by fittings disposed on the EMG sensors and/or on an inner surface of the liner. For example, as shown in FIG. 2C, the substrate 202 can define one or more openings 214 that can be configured to receive a fitting disposed along an inner surface of a liner. As further shown in FIG. 7A, a liner 530 can include one or more projections 540a, 540b configured to engage with respective openings 514a, 514b of an electrode portion 506 of the sensor. Alternatively, or in addition, one or more projections 540c can be disposed to engage with respective opening(s) 514c at an elongated portion 504 of the sensor. While FIG. 7A illustrates the fittings as being projections extending from an inner surface of the liner, the fittings can instead be disposed at the sensor. For example, as shown in FIG. 7B, the substrate 502 can include projections 516a, 516b extending from a bottom surface of the sensor (i.e., a surface opposite that of the exposed electrodes 510a, 510b) that engage with complementary receptacles 542a, 542b at an inner surface of the liner 530.

Figure 7B:
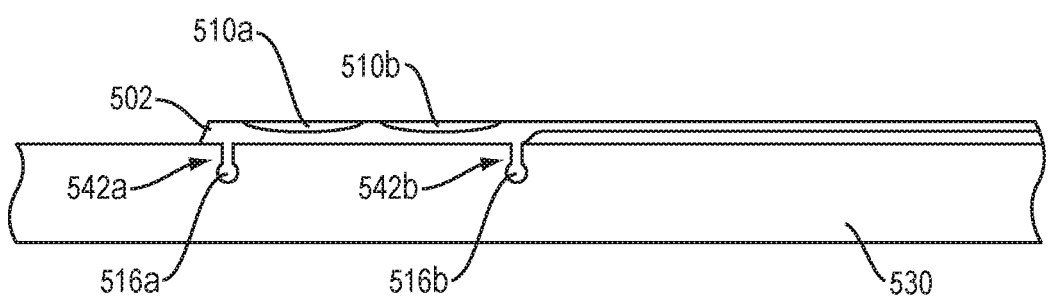
FIG. 7B shows an alternative configuration of fasteners for securing an EMG sensor to a liner.

Fittings, such as those shown in FIGS. 7A and 7B, can provide for removeable attachment of an EMG sensor to a liner, thereby enabling a user to remove the EMG sensor prior to washing the liner, while also ensuring that the EMG sensor is properly positioned within the liner during wear. While the fittings shown in FIGS. 7A and 7B are shown to be projections having a mushroom-head connector, other fitting types can instead be included on the sensor and/or the liner, such as, for example, complimentary flexible connectors of other shapes, snaps, hook-and-loop fasteners, and other re-closable fasteners.

Figure 8:
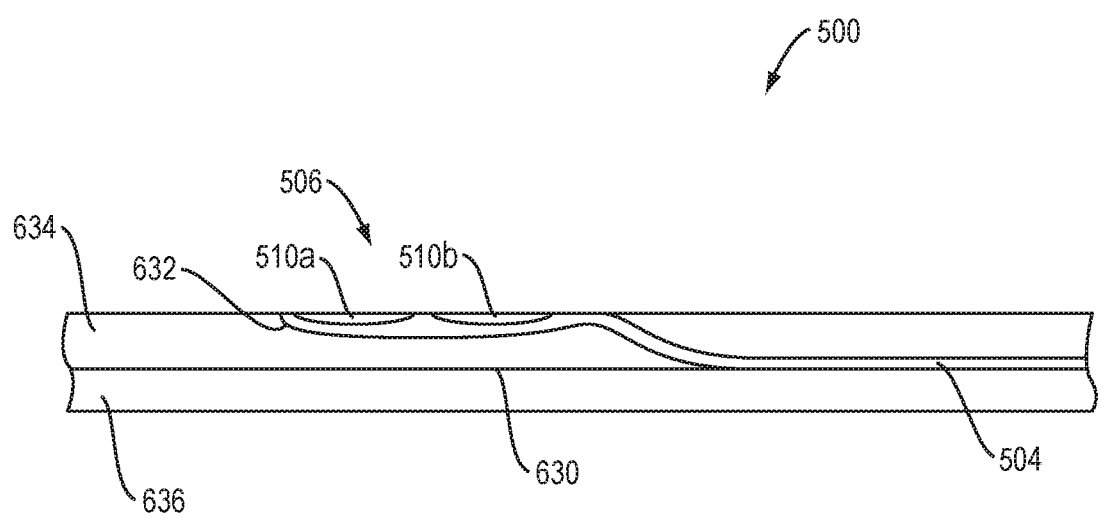
FIG. 8 shows an EMG sensor disposed within a liner.

EMG sensors, such as sensors 200, 300, 500, can instead be included in custom liners. A custom liner 630 is shown in FIG. 8 with the electrode portion 506 of the sensor positioned within a recess 632 of the liner and electrodes 510a, 510b exposed for skin contact. The elongated portion 504 of the sensor can be disposed within an interior of the liner 630, for example, sandwiched between an inner layer 634 and an outer layer 636 of liner material. The low-profile of the EMG of the sensor allows for its integration within the liner material with minimal or no interference to the cushioning provided by the liner to the wearer. Furthermore, with the EMG sensor having a connector (e.g., connector 208, FIG. 2A) configured to be positioned outside of the liner and socket, other EMG-related electronics (e.g., portable sEMG device 536, FIG. 5) can be decoupled from the liner, allowing for easier washing and more frequent replacement of the liner at a lower cost, as compared with other custom liners.

Figure 9:
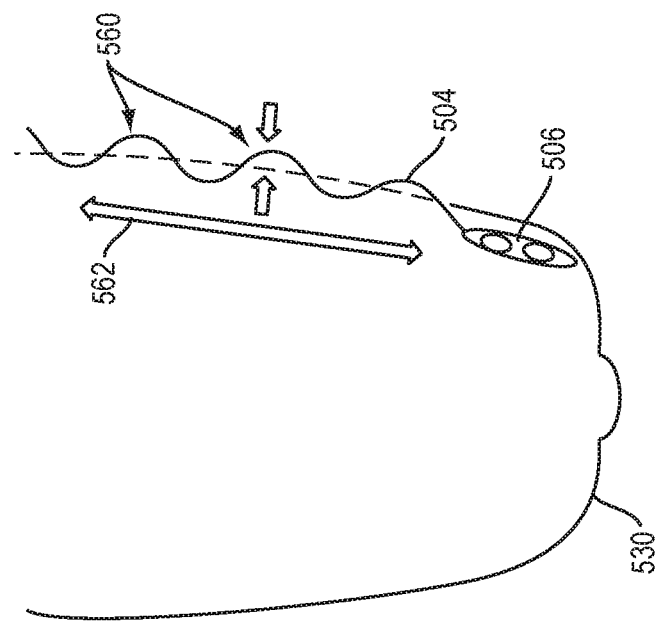
FIG. 9 shows an expandable EMG sensor.
Figure 9:
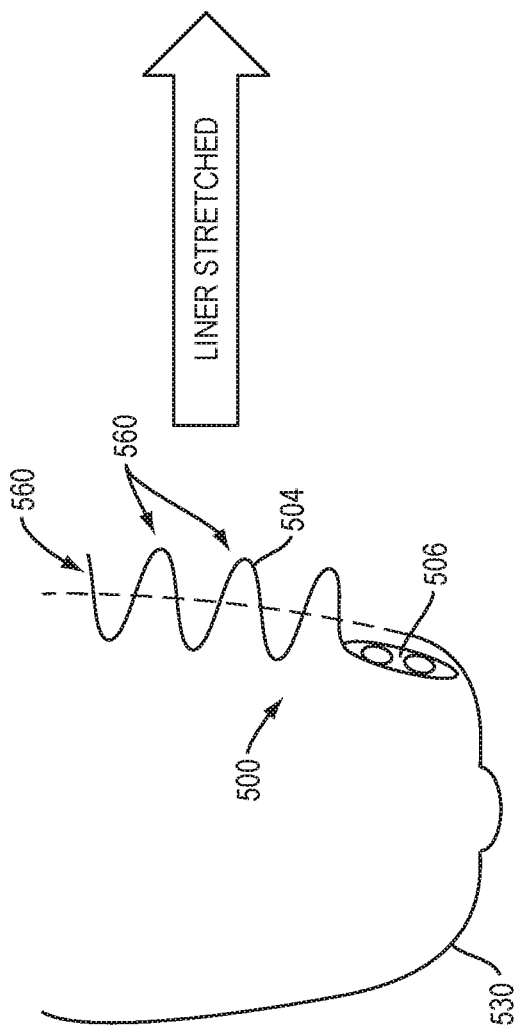

Liners for prosthetic devices are typically flexible, allowing for a sock-like fit over a residual limb, and are typically stretched during donning. To prevent stretching of a liner from interfering with placement of EMG sensors within the liner, an elongated portion of the EMG sensor can be disposed in a serpentine or corrugated shape, thereby allowing for extension during stretching of the liner. As shown in FIG. 9, the elongated portion 504 of the EMG sensor 500 is disposed within a liner 530 such that it includes a series of reciprocating bends or folds 560. Upon stretching of the liner in the direction shown by arrow 562, the folds 560 permit the elongated portion 504 of the sensor to extend along the same direction as the liner without disrupting a position of the electrode portion 560.

Figure 10:
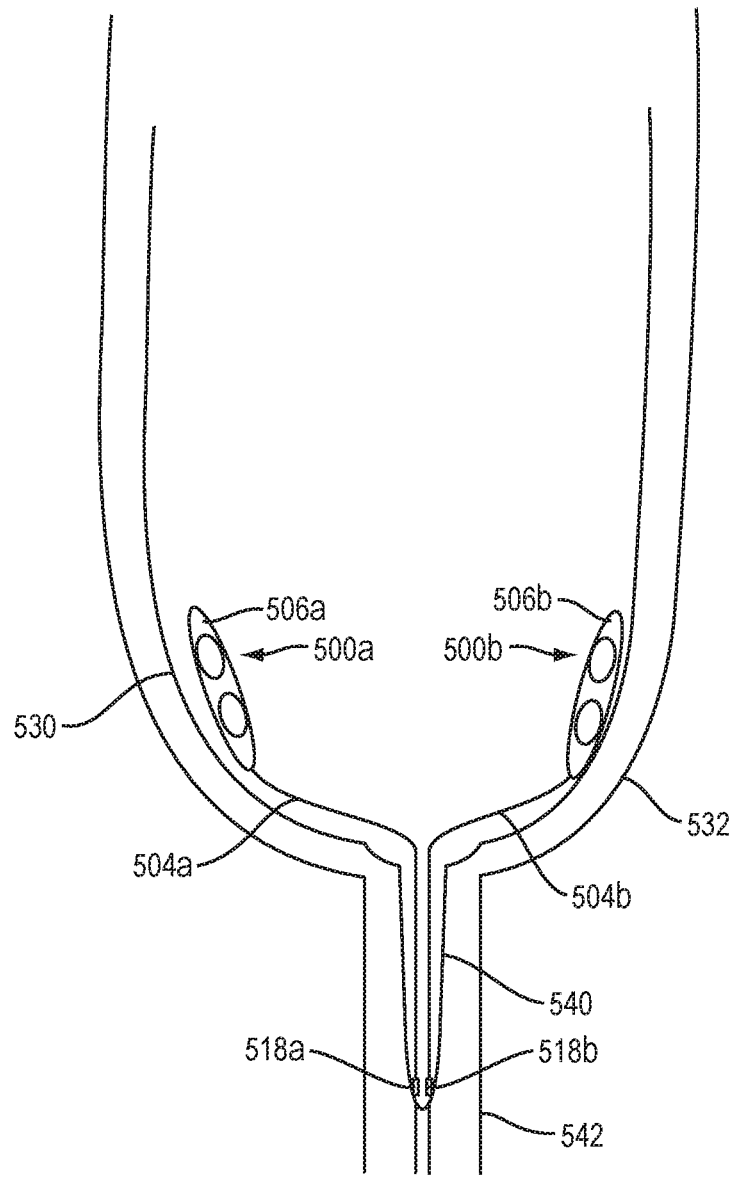
FIG. 10 shows a schematic illustrating an alternative placement of an EMG sensor in a prosthetic liner.

In an alternative configuration to that shown in FIG. 5, EMG sensors can be configured to communicate with an actuator of a prosthetic device through a pin-lock connection between a liner and/or socket and the prosthetic device. As shown in FIG. 10, elongated portions 504a, 504b of EMG sensors 500a, 500b are disposed to extend towards a distal end of the liner 530. As illustrated, the liner 530 includes a pin connector 540, which is received within a pylon 542 of a prosthetic device. The elongated portions 504a, 504b can extend into the pin connector 540. Connectors 518a, 518b can be included at the pin connector 540 for communicatively coupling leads of the sensors 500a, 500b to other electronic devices disposed at or within the prosthetic device. Such a configuration can provide for hardwiring of the EMG sensors to the prosthetic device.

Figure 11:
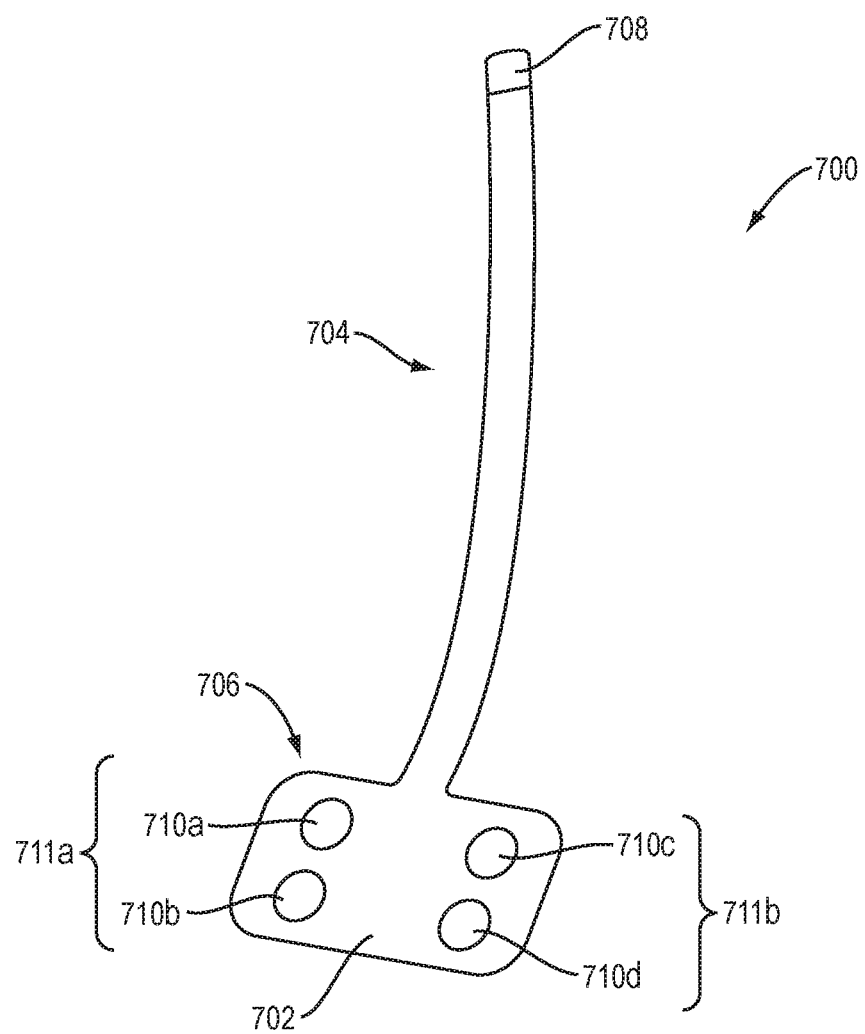
FIG. 11 shows an EMG sensor having multiple pairs of electrodes.

While EMG sensors 200, 300, 500 are illustrated as including two electrodes, more than two electrodes can be included at an electrode portion of a sensor. For example, as shown in FIG. 11, an EMG sensor 700 can include two pairs 711a, 711b of electrodes, the electrodes 710a-d disposed at the electrode portion 706 of the substrate 702. Leads (not shown) from each of the electrodes can extend through the elongated portion 704 of the substrate 702 to a connector 708.

Figure 12:
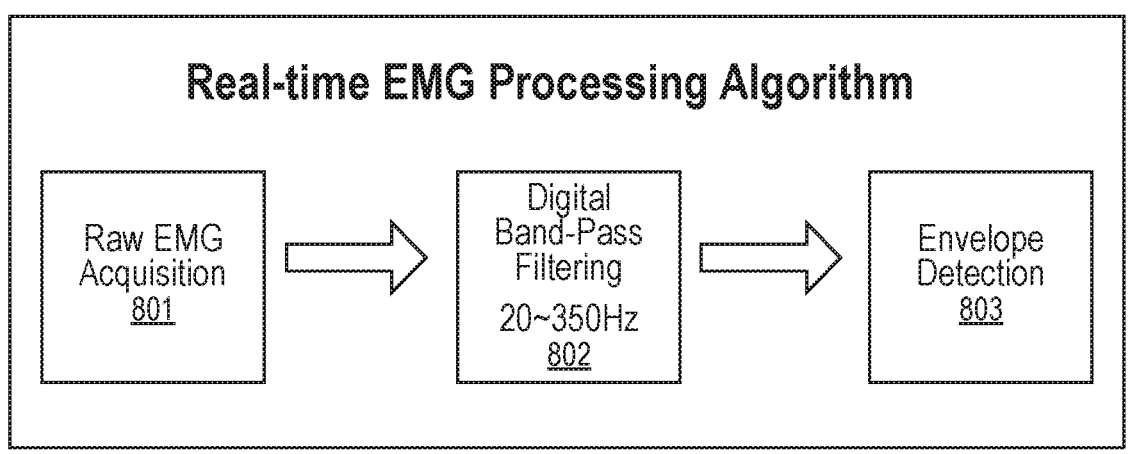
FIG. 12 is a diagram illustrating an algorithm for real-time sEMG processing.

EMG sensors, such as sensors 200, 300, 500, 700, can be configured for use with other components of a portable sEMG system, which can be disposed on or in a prosthetic socket or prosthetic device, such as sEMG device 536 (FIG. 5). By integrating portable and real-time sEMG measurement systems to an active powered prosthetic system, it is possible to deliver a portable prosthesis with neural control. The sEMG system can, through sensors 200, 300, 500, 700, capture electrical activities of muscles of a residual limb or other body segment and process the captured activity to estimate relative muscle activations. FIG. 12 illustrates an example algorithm 800 for real-time processing of sEMG signals, including raw EMG acquisition 801, filtering 802, and envelope detection 803. Electronics configured to provide for steps 802 and 803 can be decoupled from an EMG sensor, thereby minimizing electronic components disposed on or at a liner of a prosthetic device. The estimated muscle activations obtained from process 800 can be fed into a high-level dynamic controller to generate torque, velocity, and position profiles for an actuator of the prosthetic device.

Figure 13:
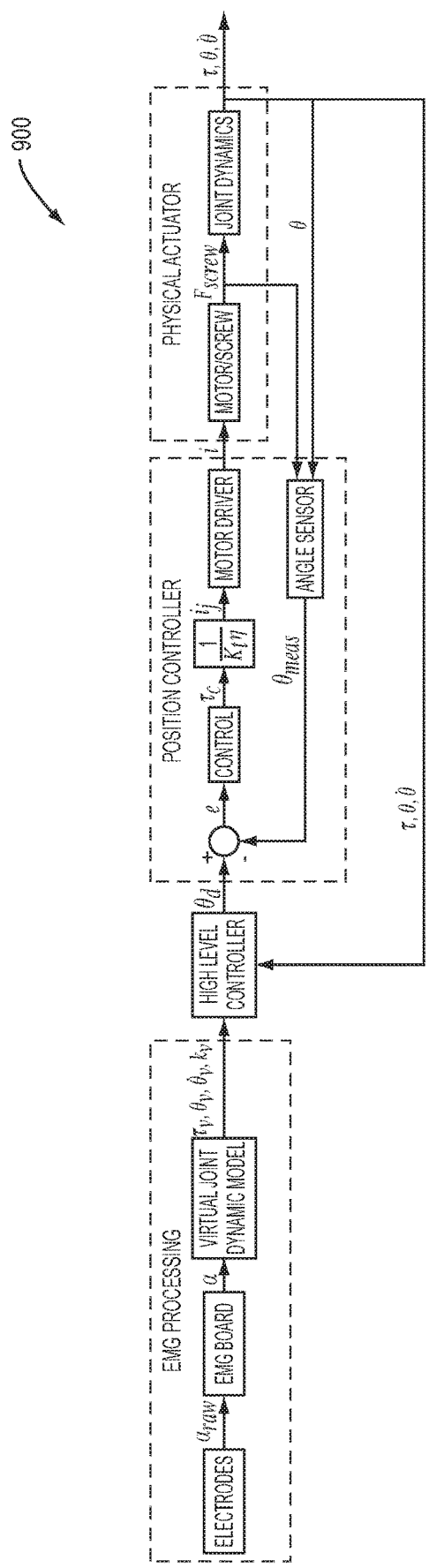
FIG. 13 is a diagram illustrating a control system for processing detected muscle activation levels to provide input to a powered prosthetic device.

An example of a control system 900 that can be used with EMG input from a portable EMG device is outlined in FIG. 13. In particular, the EMG input may be used to control the prosthetic device via machine learning, proportional control, or a plurality of mathematical biomechanical models. An example of EMG input processing includes virtual joint dynamic modeling. The details of this model are shown in FIG. 14A. Using this control approach, EMG signal amplitudes recorded from agonist and antagonist muscles are interpreted as desired torques produced in opposite directions about a virtual dynamic joint, constructed with physiologically-relevant values for virtual parallel spring stiffness, virtual damping, and virtual inertia. The difference of these estimated torques can then applied to the virtual joint, causing it to move. A position of the virtual joint can then control a desired position of an associated prosthetic joint. Prosthetic joint stiffness can be directly modulated by a mean activation of the agonist and antagonist muscles. Such control architecture can enable independent modulation of joint position and impedance. A benefit to the virtual joint architecture shown in FIG. 14A is that filter parameters can take on intuitive physical meaning and can be set to near-physiologic values. The control architecture of FIG. 13 can also be used with functional electrical stimulation feedback, an example of which is shown in FIG. 14B.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An electromyography sensor for a wearable device comprising:
   a flexible substrate comprising an elongated portion and an electrode portion;
   at least two electromyography electrodes disposed at a surface of the electrode portion of the flexible substrate, a thickness of the electrode portion of the flexible substrate and the at least two electromyography electrodes being in the range of about 50 µm to about 500 µm;
   leads extending from the at least two electromyography electrodes through the elongated portion of the flexible substrate; and
   connectors at the end of the leads;
   the electromyography sensor configured to be positioned within a prosthetic liner to be fit over a residual limb with the two electromyography electrodes facing inwardly to contact skin of the residual limb, the elongated portion extending along the prosthetic liner to position the connectors to be engaged with and decoupled from electromyography electronics associated with a prosthetic socket positioned over the liner and residual limb.

2. A liner for a prosthetic socket comprising:
   compressible liner material configured to be fit over a residual limb and disposed between the limb and the prosthetic socket; and
   an electromyography sensor comprising:
      a flexible substrate comprising an elongated portion and an electrode portion;
      at least two electromyography electrodes disposed at a surface of the electrode portion of the flexible substrate;
      leads extending from the at least two electrodes through the elongated portion of the flexible substrate; and
      connectors at the end of the leads;
   the electromyography sensor positioned within the compressible liner material with the two electromyography electrodes facing inwardly to contact skin of the residual limb, the elongated portion extending along the prosthetic liner material to position the connectors to be engaged with and decoupled from electromyography electronics associated with the prosthetic socket.

3. The liner of claim 2 wherein a thickness of the electrode portion of the flexible substrate and the at least two electrodes is in the range of about 50 µm to about 500 µm.

4. The liner of claim 2 wherein a thickness of the electrode portion of the flexible substrate and the at least two electrodes is in the range of about 50 µm to about 120 µm.

5. The liner of claim 2 wherein the at least two electrodes are dry, passive electrodes.

6. The liner of claim 2 wherein each of the at least two electrodes comprises a flexible metal layer, the flexible substrate and the flexible metal layers configured to conform to a skin surface.

7. The liner of claim 2 wherein the at least two electrodes are disposed at a relative center-to-center distance in the range of about 1 cm to about 4 cm.

8. The liner of claim 2 wherein the at least two electrodes are disposed at a relative center-to-center distance in the range of about 1.5 cm to about 2 cm.

9. The liner of claim 2 wherein a diameter of each the at least two electrodes is in the range of about 0.5 cm to about 1.5 cm.

10. The liner of claim 2 wherein the substrate is non-woven.

11. The liner of claim 2 wherein the substrate comprises a flexible polymer.

12. The liner of claim 2 wherein the substrate comprises polyimide.

13. The liner of claim 2 wherein the electromyography sensor is adhered to an inner surface of the liner material.

14. The liner of claim 2 wherein an inner surface of the liner material comprises a recess configured to receive the electrode portion of the electromyography sensor.

15. The liner of claim 2, wherein at least one of the electromyography sensor and the liner material comprises a fastener configured to fasten the electromyography sensor to an inner surface of the liner material.

16. The liner of claim 15, wherein the flexible substrate of the electromyography sensor comprises a plurality of holes configured to receive complimentary projections disposed within the inner surface of the liner material.

17. The liner of claim 2, wherein the elongated portion of the electromyography sensor is disposed between an inner layer and an outer layer of the liner material, the elongated portion comprising a serpentine or corrugated shape configured to extend upon stretching of the liner material.

18. The liner of claim 2, wherein the elongated portion of the electromyography sensor is disposed to extend over a proximal end of the liner material.

19. The liner of claim 2, wherein the elongated portion of the electromyography sensor is disposed to position the connectors to at a distal end of the liner material to make electrical connection with the prosthetic socket.

20. The liner of claim 2, wherein the elongated portion of the electromyography sensor is disposed to position the connectors to engage with a portable electromyography device in communication with the prosthetic socket.

21. A method of processing electromyography signals from a residual limb comprising:
   placing the liner of claim 2 over the residual limb with the electromyography electrodes contacting skin of the residual limb;
   placing a prosthetic socket over the liner and residual limb;
   engaging the connectors with electromyography electronics; and processing electromyography signals from the electromyography electrodes in the electromyography electronics.

22. The method of claim 21 further comprising controlling a prosthetic device that includes the prosthetic socket with the processed electromyography signals.

* * * * *